United States Patent
Davenport et al.

(10) Patent No.: US 6,554,824 B2
(45) Date of Patent: Apr. 29, 2003

(54) METHODS FOR LASER TREATMENT OF SOFT TISSUE

(75) Inventors: Scott Davenport, Half Moon Bay, CA (US); Steven C. Murray, Santa Cruz, CA (US); Tony Coleman, San Jose, CA (US)

(73) Assignee: Laserscope, San Jose, CA (US)

(*) Notice: Subject to any disclaimer, the term of this patent is extended or adjusted under 35 U.S.C. 154(b) by 221 days.

(21) Appl. No.: 09/737,721

(22) Filed: Dec. 15, 2000

(65) Prior Publication Data

US 2003/0018324 A1 Jan. 23, 2003

(51) Int. Cl.[7] ............................................. A61B 18/18
(52) U.S. Cl. ........................... 606/3; 606/2; 606/15; 600/2; 607/89; 607/100
(58) Field of Search ..................... 606/3, 2, 10, 11, 606/12, 16, 17, 7, 15, 27, 28, 29, 30, 31; 600/2, 3; 607/89, 90, 92, 100, 101, 102

(56) References Cited

U.S. PATENT DOCUMENTS

| | | | |
|---|---|---|---|
| 4,646,737 A | | 3/1987 | Hussein et al. |
| 4,981,138 A | * | 1/1991 | Deckelbaum et al. ....... 600/478 |
| 5,151,909 A | | 9/1992 | Davenport et al. |
| 5,243,615 A | | 9/1993 | Ortiz et al. |
| 5,249,192 A | | 9/1993 | Kuizenga et al. |
| 5,257,991 A | | 11/1993 | Fletcher et al. |
| 5,312,392 A | * | 5/1994 | Hofstetter et al. ............. 606/2 |
| 5,409,481 A | | 4/1995 | Poppas et al. |
| 5,451,221 A | * | 9/1995 | Cho et al. ...................... 606/3 |
| 5,495,541 A | * | 2/1996 | Murray et al. ................ 606/17 |
| 5,628,744 A | | 5/1997 | Coleman et al. |
| 5,632,739 A | * | 5/1997 | Anderson et al. .............. 606/2 |
| 5,746,760 A | | 5/1998 | Humphrey, Jr. |
| 5,776,127 A | * | 7/1998 | Anderson et al. .............. 606/2 |
| 5,776,175 A | * | 7/1998 | Eckhouse et al. ........... 607/100 |
| 5,778,395 A | | 7/1998 | Whiting et al. |
| 5,798,518 A | | 8/1998 | Coleman et al. |
| 5,841,800 A | | 11/1998 | Davenport et al. |
| 5,843,026 A | | 12/1998 | Edwards et al. |
| 6,024,751 A | | 2/2000 | Lovato et al. |
| 6,064,914 A | | 5/2000 | Trachtenberg |
| 6,389,313 B1 | * | 5/2002 | Marchitto et al. ............ 607/92 |
| 6,423,055 B1 | * | 7/2002 | Farr et al. ..................... 606/15 |

OTHER PUBLICATIONS

C T W Lahaye, et al. "Optimal Laser Parameters for Port Wine Stain Therapy: A Theoretical Approach", Phys. Med. Biol., vol. 30, No. 6, pp. 573–587, 1985.

Orazio Svelto, Principles of Lasers Fourth Edition pp. 480–482, Plenum Press, New York, NY, 1998.

Randall S. Kuntzman, et al., "High–Power (60–Watt) Potassium–Titanyl–Phosphate Laser Vaporization Prostatectomy in Living Canines and in Human and Canine Cadavers", Urology, vol. 49, No. 5, pp. 703–708, Elsevier Science, Inc. 1997.

Nicolas Mottet, M.D., Ph.D., et al. "Randomized Comparision of Transurethral Electroresection and Holmium: YAG Laser Vaporization for Symptomatic Benign Prostatic Hyperplasia", Journal of Endourology, vol. 13, No. 2, Mar. 1999, pp. 127–130, Mary Ann Liebert, Inc.

(List continued on next page.)

Primary Examiner—Teresa Walberg
Assistant Examiner—Fadi H. Dahbour
(74) Attorney, Agent, or Firm—Mark A. Haynes; Haynes Beffel & Wolfeld LLP

(57) ABSTRACT

Methods are provided for treating prostate glands or other targeted soft tissue using a solid-state laser. The laser can be operated to generate a pulsed output beam having pulse durations of between 0.1 and 500 milliseconds. The output beam is delivered to the targeted tissue through an optical fiber, preferably terminating in a side-firing probe or diffusing tip. By operating the laser in a long-duration pulse mode, charring of the targeted tissue is initiated quickly, thereby increasing ablation rates and reducing overall procedure time.

45 Claims, 4 Drawing Sheets

OTHER PUBLICATIONS

P.A. Conford, et al., "Transurethral Incision of the Prostate Using the Holmium: YAG Laser: a Catheterless Procedure", The Journal of Urology, vol. 159, Apr. 1998, pp. 1229–1231, American Urological Association, Inc.

Rosenfeld, Harold, et al. "Treatment of Cutaneous and Deep Vascular Lesions with the Nd:YAG Laser", Lasers in Surgery and Medicine, vol. 6, pp. 20–23, 1986.

Reza S. Malek, et al., "High Power Potassium–Titanyl–Phosphate Laser Vaporization Prostatectomy", The Journal of Urology, vol. 163, Jun. 2000, pp. 1730–1733, American Urological Association, Inc.

Peter J. Gilling, et al., "Combination Homium and Nd:YAG Laser Ablation of the Prostate: Initial Clinical Experience", Journal of Endourology, vol. 9, No. 2, Apr. 1995, Mary Ann Liebert, Inc., Publishers.

Peter J. Gilling, et al., "Holmium Laser Versus Transurethral Resection of the Prostate: a Randomized Prospective Trial with 1–Year Followup", The Journal of Urology, vol. 162, Nov. 1999, pp. 1640–1644, American Urological Association.

Reza S. Maleck, et al., "High–Power Potassium–Titanyl–Phosphate (KTP/532) Laser Vaporization Prostatectomy: 24 Hours Later", Urology, vol. 51, No. 2, pp. 254–256, Elsevier Science, Inc. 1998.

Peter Gilling, "Holmium Laser Resection of the Prostate Versus Neodymium:Yttrium–Aluminum–Garnet Visual Laser Ablation of the Prostate: Randomized Prospective Comparision of Two Techniques for Laser Prostatectomy", Urology, vol. 51, No. 4, pp. 573–577, Elsevier Science, Inc. 1998.

J.A. Dixon, M.D. et al., "Argon and Neodymium YAG Laser Therapy of Dark Nodular Port Wine Stains in Older Patients", Lasers in Surgery and Medicine, vol. 6, pp. 5–11, Alan R. Liss, Inc., 1986.

Martin J.C. Van Gemert, Ph.D, et al., "Treatment of Port–Wine Stains: Analysis" Medical Instrumentation, vol. 21, No. 4, pp. 213–217, Association for the Advancement of Medical Instrumentation, 1987.

Martin J.C. Van Gemert, Ph.D, et al., "Is there an Optimal Laser Treatment for Port Wine Stains?" Lasers in Surgery and Medicine, vol. 6, pp. 76–83, Alan R. Liss, Inc., 1986.

M. Lanthaler, M.D., et al., "Effects of Argon, Dye and Nd: YAG Lasers on Epidermis, Dermis, and Venous Vessels" Lasers in Surgery and Medicine, vol. 6, pp. 87–93, Alan R. Liss, Inc., 1986.

Carie T. Chui, M.D., et al., "Long–Pulsed Nd:YAG for Hair Removal: Early Histological Changes" LaserNews.net, LLC, 1999.

Moretti, Michael, "Laserscope's Lyra Laser Proves Multi–Functional" Aesthetic Buyers Guide, Medical Insight, Inc., Jul. 2000.

"The Lyra Laser System from Laserscope: Long–pulse Nd:YAG Laser Proven in Cosmetic Treatments" Medco Forum, vol. 7, No. 2, Mar. 2000.

"Laserscope Announces FDA Clearance for Pseudo–Folliculitis" Laserscope.com/news/021401.htm, Feb. 14, 2001 pp. 1–2.

"Laserscope Announces PMA Application to U.S. Food and Drug Administration for PDT Treatment of Head and Neck Cancer" Laserscope.com/news/110999.htm, Nov. 9, 1999, pp. 1–2.

"Laserscope Engouraged by Clinical Study Using New Lyra Laser System to Treat Leg Veins" Laserscope.com/news/120799.htm, Dec. 7, 1999, pp. 1–2.

"Laserscope Announces High Power Lyra Laser System: Lyra XP, AAD to be Introduced at the ADD" Laserscope.com/news/030800.htm, Mar. 8, 2000, pp. 1–2.

"Laserscope Receives FDA Clearance to Market New LYRA Laser System for Hair Removal: First laser Designed for Full Range of Skin Types" Laserscope.com/news/031300.htm, Mar. 13, 2000, pp. 1–3.

"Laserscope Reports First Quarter 2000 Results" Laserscope.com/news/050400.htm, May. 4, 2000, pp. 1–3.

"Laserscope Announces Approvable Letter Received for PDT Laser System for the Treatment of Head and Neck Cancer" Laserscope.com/news/052200.htm, May 22, 2000, pp. 1–2.

"Researchers Report Decidedly Positive Two–Year Results Using Laserscope's Ultra–High Power Laser and Disposable Fiber Optics to Treat BPH: Researchers Call the Results Unprecedented" Laserscope.com/news/060800.htm, Jun. 8, 2000, pp. 1–2.

"Laserscope Announces a Winner of the Palm Pilot Drawing" Laserscope.com/news/100300.htm, Sep. 29, 2000, p. 1.

"Laserscope Reports Increased Profits in Third Quarter 2000 Results" Laserscope.com/news/101900.htm, Oct. 19, 2000, pp. 1–3.

"Laserscope Signs Exclusive Agreement with McKessonHBOC Medical Group for National Distribution of Aesthetic Laser Systems" Laserscope.com/news/121400.htm, Dec. 14, 2000, pp. 1–2.

"Laserscope Reports Fourth Quarter and Year End 2000 Results" Laserscope.com/news/021301.htm, Feb. 13, 2001, pp. 1–3.

Kollmorgen, Thomas A. et al., "Laser Prostatectomy: Two and a Half Years' Experience with Aggressive Multifocal Therapy" Urology, vol. 48, pp. 217–222, 1996, Elsevier Science, Inc.

Kuntzman, Randall S., MD et al., "High–Power Potassium Titanyl Phosphate Laser Vaporization Prostatectomy", Mayo Clinic Proc., vol. 73. pp. 798–801, 1998.

Kuntzman, Randall S., MD et al., "Potassium–Titanyl–Phosphate Laser Vaporization of the Prostate: A Comparative Functional and Pathologic Study in Canines", Urology, vol. 48, pp. 575–583, 1996.

van Swol, Christiaan F.P. et al., "Physical Evaluation of Laser Prostatectomy Devices", Lasers in Urology, SPIE Bellingham, vol. 2129 (1994), 8 pgs.

U.S. patent application Ser. No. 09/569,595, Steven Murray, Variable Pulse Duration, Adjustable Wavelength Medical Laser System, filed May 9, 2000.

U.S. patent application Ser. No. 09/589,675, Steven Murray, A Device for Irradiating Tissue, filed Jun. 7, 2000.

* cited by examiner

METHODS FOR LASER TREATMENT OF SOFT TISSUE

BACKGROUND

1. Field of the Invention

The present invention relates generally to laser treatment of soft tissue, and more particularly to laser treatment of the prostate.

2. Description of the Prior Art

Benign Prostatic Hyperplasia (BPH) is a condition wherein continued growth of the prostate restricts the passage of urine through the lower portion of the bladder and the urethra. BPH is often treated by surgically removing excess prostate tissue from the transitional zone of the prostate that is pressing on the urethra, which usually relieves the bladder outlet obstruction and incomplete emptying of the bladder caused by the BPH.

Recently, the most commonly employed procedure for removal of excess prostate tissue has been transurethral resection of the prostate, also known as TURP. In the TURP procedure, the surgeon utilizes a standard electrical cutting loop to shave off small pieces of the targeted tissue from the interior of the prostate. At the end of the operation, pieces of excised prostate tissue are flushed out of the bladder using an irrigant.

While effective, the TURP procedure is known to cause numerous side effects, including incontinence, impotence, retrograde ejaculation, prolonged bleeding and TUR syndrome. Recently, alternative procedures have been developed which reduce or avoid the side effects associated with TURP. One class of procedures involves "cooking" prostate tissue by heating it to a to a temperature above 45 degrees Celsius. Typically this is accomplished using electrically resistive elements such as: radio frequency (RF), microwave, or long-wavelength lasers. An example of a procedure of this nature is discussed in U.S. Pat. No. 6,064,914 by Trachtenberg ("Thermotherapy Method"). Because these procedures leave the thermally-treated tissue in place, post-procedure edema, dysuria, and retention rates are relatively high. Further, use of thermal procedures requires the patient to be catheterized for several days following the procedure, and may cause extensive and unpredictable scarring of the intra prostatic urethra.

Another class of procedures involves vaporizing or ablating the targeted tissue using laser light. These procedures generally avoid the high infection rates and scarring problems of thermally-based procedures. However, laser ablation of prostate tissue has to date, required the use of an expensive laser capable of generating high-power laser light. The high cost of purchasing or leasing such a laser results in a concomitant increase in the cost of the procedure. Finally, the ablation process typically occurs slowly, resulting in a lengthy procedure time.

The Ho:YAG laser and its fiberoptic delivery system is an example of a laser that is commonly used for ablating prostate tissue. The Ho:YAG laser generates pulses of 2100 nm light that are strongly absorbed by water in the prostate tissue and in the saline irrigant positioned between the distal end if the fiberoptic and the tissue. The absorption coefficient of water is so high at 2100 nm that 50% of the light is absorbed within 0.2 mm. Consequently even a thin layer of irrigant positioned between the distal end on the fiberoptic and the tissue will absorb a large fraction of the laser light. Furthermore with the short pulse durations (Tp<0.5 ms) and large pulse energies (Ep>1.0 joule) used for ablating prostate tissue the irrigant is explosively boiled creating a shock wave that tears tissue. Because water is such a large constituent of prostate tissue and blood, there is essentially no selective absorption by blood. This combination of violent tissue disruption and the superficial unselective light penetration leads to poor hemostasis.

Nd:YAG lasers operating at 1064 nm have also been used for ablating prostate tissue. Although 1064 nm light is hemostatic at high power levels its low absorption in blood and prostate tissue leads to inefficient ablation and a large residual layer of thermally denatured tissue several millimeters thick. After surgery the thermally denatured tissue swells and leads to transient urinary retention, which can cause long catheterization times, painful urination, and high infection rates.

Frequency doubled Nd:YAG lasers operating at 532 nm in a Quasi continuous mode at power levels up to 60 watts have been used to efficiently and hemostatically ablate prostate tissue. These lasers are pumped by CW krypton arclamps and produce a constant train of Q-switched pulses at 25 kHz. The high Q-Switch frequency makes the tissue effects indistinguishable from CW lasers of the same average power. The 532 nm light from these lasers is selectively absorbed by blood leading to good hemostasis. When ablative power densities are used, a superficial layer of denatured prostate tissue less than 1 mm is left behind. This thin layer of denatured tissue is thin enough that the immediate post surgical swelling associated with other treatment modalities is greatly reduced. This reduced swelling leads to short catheterization times and less dysuria. At high powers, 532 nm lasers induce a superficial char layer (an absorptive, denatured layer) that strongly absorbs the laser light and greatly improves the ablation efficiency. The problem with the existing 532 nm lasers used to date is that they are large, expensive, inefficient, and have a highly multi-mode output beam that makes them inefficient for ablating prostate tissue.

High power densities are required for rapid and efficient vaporization of prostate tissue. The difficulty of achieving higher average output power densities is that when high input powers are supplied to the laser element from an excitation source such as an arclamp a large amount of heat is generated in the lasing element. This heat induces various deleterious effects in the lasing element. In particular the temperature difference between the coolant and the hot lasing element generates a thermally induced graded index lens that decreases the beam quality of the laser and causes the laser to operate with more transverse optical modes than it would otherwise.

The $M^2$ parameter is a well established convention for defining the beam quality of a laser and is discussed in pages 480–482 of Orazio Svelto and David C. Hanna, *Principles of Lasers*, Plenum Press, New York, 1998, which is incorporated herein by reference. The beam quality measures the degree to which the intensity distribution is Guassian. The quantity $M^2$ is sometimes called inverse beam quality rather than beam quality but in this application it will be referred to as beam quality. $M^2$ is defined as $$M_x^2 \equiv \frac{(\sigma_x \sigma_f)_{NG}}{(\sigma_x \sigma_f)_G} = 4\pi(\sigma_x \sigma_f)_{NG},$$

where $\pi$ refers to the number 3.14 . . . , $\sigma$ is used to represent the spot size, the subscripts x and f represent the spatial and frequency domains along the x-axis, respectively, and the subscripts G and NG signify Guassian and non-Guassian, respectively. The x-axis is transverse to the direction of propagation of the beam. The beam quality in any direction transverse to the beam may be essentially the same. Therefore the subscript x is dropped from the $M^2$ elsewhere in the specification. The beam widths or σs are determined based on the standard deviation of the position, where the squared deviation of each position is weighted by the intensity at that point. The beam width in the frequency domain $\sigma_f$ is the beam width of the beam after being Fourier transformed.

The formula usually used for calculating the angular divergence, θ, of a beam of light of wavelength λ is strictly valid only for a beam having a Guassian intensity distribution. The concept of beam quality facilitates the derivation of the angular divergence, θ, for the beam with a non-Guassian intensity distribution, according to $$\theta = M^2 \left( \frac{2\lambda}{\pi \sigma_x} \right).$$

For example, a TEM00 laser beam has a high beam quality with an $M^2$ of 1, whereas by comparison, high power surgical lasers operate with $M^2$ values greater than 100.

The Applicants have recognized that high power lasers typically have an $M^2 > 144$. The larger number of modes makes $M^2$ larger and makes it difficult to focus the light into small, low numerical aperture fibers and reduces the ability to project high power density light onto tissue. As a result, the vaporization efficiency of CW arclamp pumped 532 nm lasers on prostate tissue is significantly reduced.

SUMMARY

According to one embodiment of the invention, a method for treating BPH comprises the steps of providing a solid-state laser having a laser element positioned to receive pump radiation from an excitation source; in some cases modulating the source to cause the laser to emit pulsed laser light; and delivering the laser light to targeted tissue. Various solid-state lasers may be used for this purpose, including (without limitation), a Q-switched arc lamp-pumped or a flash lamp-pumped laser using a frequency doubling crystal such as potassium-titanyl-phosphate (KTP). The pulse duration of the laser light is preferably in the range of 0.1 to 500 milliseconds, and the wavelength of the laser light is preferably between 200 and 1000 nanometers. The laser light is preferably delivered to the targeted prostate tissue through an optical fiber terminating at a distal end in a side-firing probe. However the side-firing probe is not essential.

Operation of the solid-state laser in a "macropulsed" mode is more efficient in inducing rapid tissue ablation than a CW laser of the same average power. This is in part because the macropulsing is more efficient in inducing "char" formation, a mild carbonization in which the tissue typically darkens slightly but does not necessarily turn completely black. Although char formation is not essential to efficient rapid ablation it is helpful because the darkened tissue is better at absorbing light. The macropulsed laser is also more efficient and has higher beam quality, with $M^2$ values typically less than 144, than a continuous wave laser with same average output power.

According to a second embodiment of the invention, a method for treating soft tissue comprises the steps of providing a solid-state laser having a laser element positioned to receive pump radiation from a pump radiation source; modulating the pump radiation source to cause the laser element to emit laser light having a pulse duration of between 0.1 milliseconds and 500 milliseconds and an output power exceeding 20 watts; and delivering the laser light to targeted tissue.

According to a third embodiment of the invention, a method for treating BPH comprises the steps of providing a solid-state laser having a laser element positioned to receive pump radiation from a pump radiation source; Q-switching the laser to generate a quasi-continuous wave (CW) beam having an output power exceeding 60 watts; and, delivering the beam to targeted prostate tissue.

According to a fourth embodiment of the invention, a method for treating BPH comprises the steps of providing a solid-state laser having a laser element positioned to receive pump radiation from a pump radiation source such as a laser diode; Q-switching the laser to generate a quasi-continuous wave (CW) beam having an output power exceeding 20 watts with an $M^2$ less than 144; and delivering the beam to prostate tissue.

DETAILED DESCRIPTION OF EMBODIMENTS OF THE INVENTION

Figure 1:
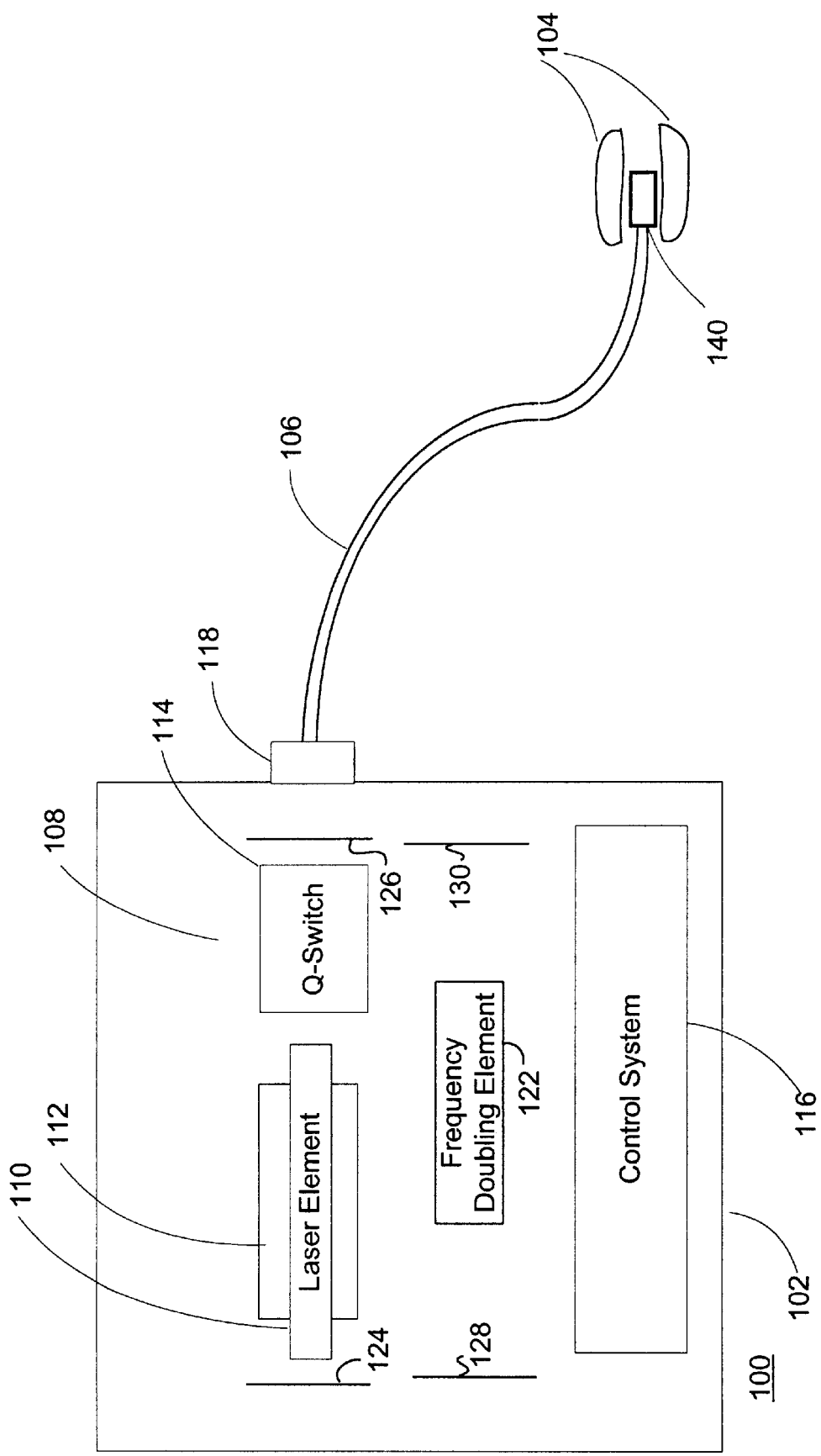
FIG. 1 depicts a laser system for implementing the tissue ablation methods of the invention.

FIG. 1 is a block diagram depicting an exemplary laser system 100 which may be employed for implementing the present invention. Laser system 100 includes a solid-state laser 102, which is used to generate laser light for delivery through optical fiber 106 to target tissue 104. As will be discussed in further detail herein below, laser 102 is capable of being operated in a "macropulsed" mode, wherein the laser light is emitted as macropulses having relatively long pulse durations.

Laser 102 more specifically comprises a laser element assembly 110, pump source 112, and frequency doubling crystal 122. In the preferred-embodiment, laser element 110 outputs 1064 nm light which is focused into frequency doubling crystal 122 to create 532 nm light. According to one implementation, laser element assembly 110 may be neodymium doped YAG (Nd:YAG)crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser 102 may be operated in a repetitive mode to cause a train of micropulses to be generated by laser 102. Typically the micropulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser 102 is provided with a control system 116 for controlling and operating laser 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm light. The frequency doubled, shorter wavelength light is better absorbed by the hemoglobin and char tissue, and promotes more efficient tissue ablation. Finally, the green light leaves only a thin char layer with little pre and post operative bleeding.

In the preferred embodiment the resonant cavity control system is that described in U.S. Pat. No. 5,151,909, incorporated herein by reference.

Laser 102 further includes an output port couplable to optical fiber 106. Output port 118 directs the light generated by laser 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window.

While a bare fiber may be utilized for certain procedures, optical fiber 106 preferably terminates in a tip 140 having optical elements for shaping and/or orienting the beam emitted by optical fiber 106 so as to optimize the tissue ablation process.

Figure 2:
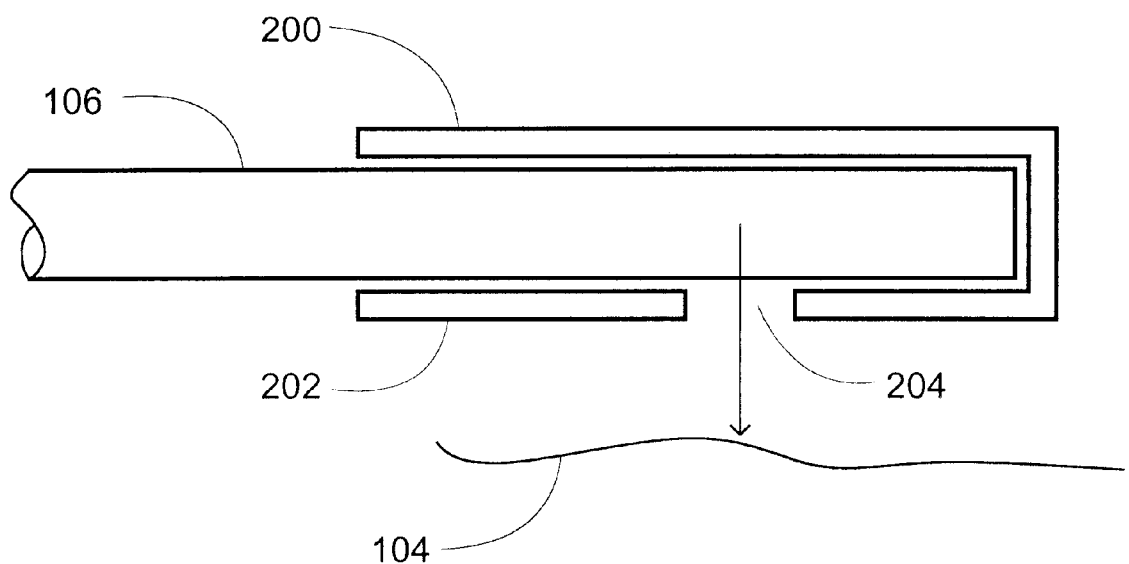
FIG. 2 depicts a side-firing probe for use with the system of FIG. 1.

FIG. 2 depicts a side-firing probe tip 200, which may be used as tip 140 (FIG. 1). The tip 140 is treated to deflect light sideways. Some examples of methods for deflecting the light sideways are to include a light scattering material in the tip 140 and/or to place a reflective element in the tip 140. The reflective element could be angled at 45°, for example; to deflect the light at 90° with respect to the axis of the fiber 106. Side-firing probe tip 200 includes an optically transparent sleeve 202 having a transparent window 204 (which may be constructed as a cutout in the wall of sleeve 202 through which the beam is emitted in a direction transverse to the optical axis of fiber 106.) An acceptable range of angles in which to deflect the light beam is between about 40 to 120 degrees with respect to the axis of the fiber. The preferred embodiments use an angle of either 70 or 100. The angle of 80° is preferred from the standpoint of the ease in manufacturing the tip 200 and the angle of 90° is preferred from the standpoint of the ease in aiming the side firing light.

In a typical mode of operation, optical fiber 106 is held within an endoscope such as a cystoscope or similar instrument that allows the clinician to precisely position the distal end of the optical fiber adjacent to the targeted tissue. The endoscope also has channels for supplying and removing an irrigant solution to and from the tissue. In addition, light and image guides are also included for illuminating and imaging the tissue so that the clinician may direct the laser light and assess the progress and efficacy of the ablation procedure.

Figure 3:
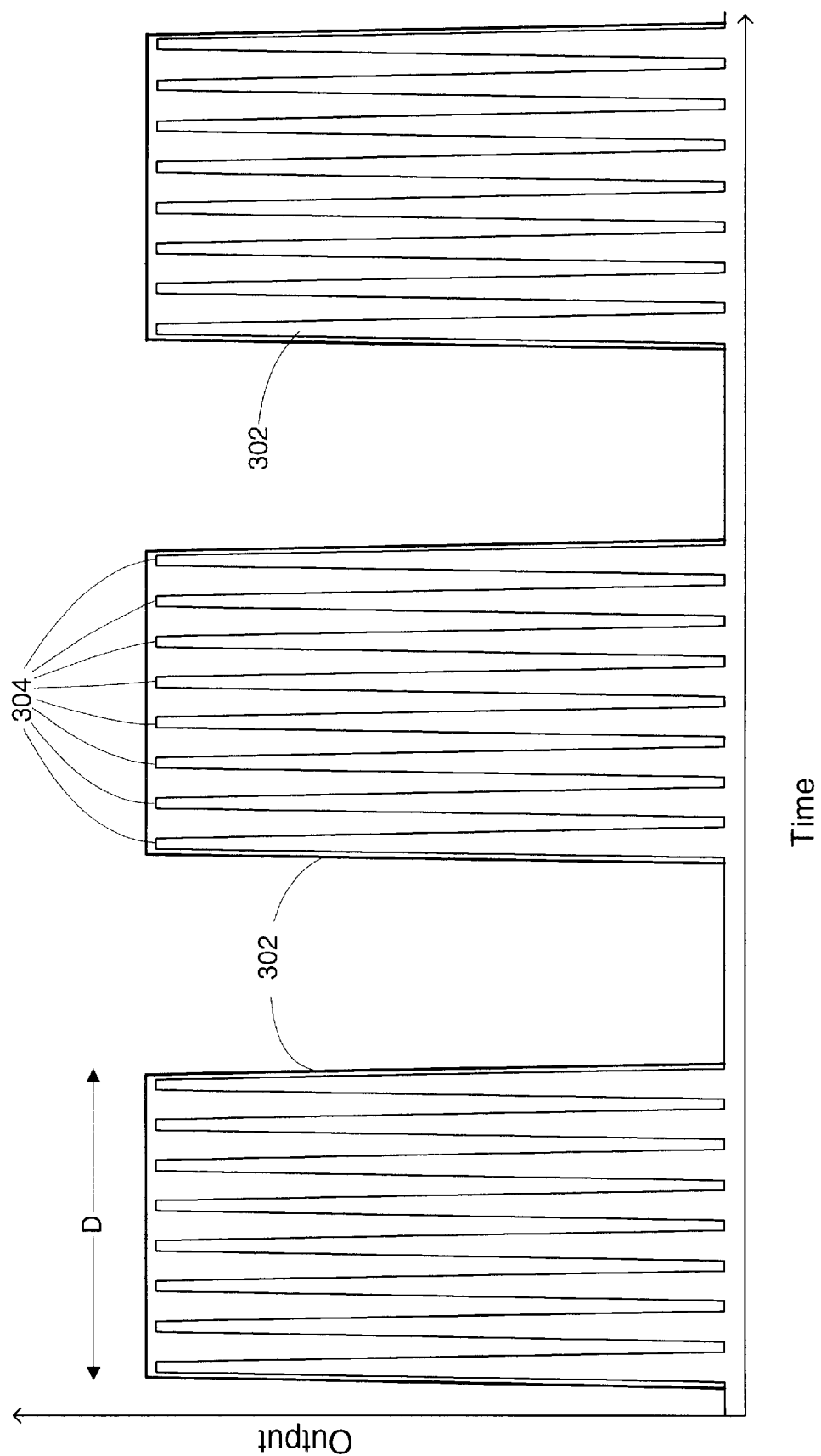
FIG. 3 depicts an exemplary output waveform of the FIG. 1 laser when the laser is operated in a macropulsed mode.

FIG. 3 illustrates an exemplary output waveform applied to tissue 104 when laser 102 is operated in the macropulsed mode. Each macropulse 302 is defined by a train of Q-switched micropulses 304. While a relatively small number of micropulses 302 are depicted for purposes of clarity, an actual macropulse may comprise hundreds or thousands of component micropulses 304. In the preferred embodiment there are between 2 and 12,200 micropulses per macropulse.

An arc lamp, for example, when used as the pump source 112, is kept at a low power level between pulses that are preferably just enough to maintain the arc. These low pump powers are below the lasing threshold of the laser; as a consequence, there is no laser output between macropulses.

As mentioned above, the pulse duration or width D (FIG. 3) of the output beam is governed by the modulation of pump source 112, and more specifically by the period during which the pump source 112 is maintained in an "on" or high-power condition. In other words, the longer the pump source 112 is maintained in an on condition, the longer the pulse width. Typically, laser 102 will be capable of delivering pulses 302 having pulse durations D in the range of 1 to 20 milliseconds (2 to 490 micropulses) or 1 to 50 milliseconds (2 to 1,220 micropulses) and average output powers preferably exceeding 60 watts and preferably up to 100 watts, and possibly up to 200 watts. The ratio of D to the period of the macropulses defines the duty cycle, which is typically between 10 and 50%.

In accordance with one embodiment of the invention, a laser system 100 of the foregoing description is employed to treat BPH by ablating targeted prostate tissue 104. The clinician may utilize an endoscope or similar instrument to guide the distal end and tip 140 of optical fiber 106 into alignment with the targeted prostate tissue 104. Laser system 100 is then operated in the macropulsed mode so that laser 102 generates laser light having the pulsed waveform depicted in FIG. 3 and delivers it through optical fiber 106 to tissue 104.

It is known that irradiation of prostate tissue 104 may initially cause tissue heating resulting in the formation of a char layer. This char layer is highly optically absorptive in the wavelengths emitted by laser 102, which thereby facilitates efficient absorption of the laser light and resultant ablation of tissue 104. However, the formation of the char layer is not essential for efficient ablation. Prior art techniques for treatment of BPH by laser ablation (such as the technique described by Kuntzman et al. in "High-Power (60-Watt) Potassium-Titanyl-Phosphate Laser Vaporization Prostatectomy in Living Canines and in Human and Canine Cadavers," *Urology,* Vol. 49, No.5 (1997)) utilized a quasi-CW laser to irradiate the prostate. Although such lasers do produce moderately high average powers, they have a large number of transverse modes and as such, produce highly divergent light when focused into small fiberoptics. This leads to less than optimal power densities when the laser light is directed at issue. As a consequence, these lasers are not particularly efficient at inducing formation of a char layer, and ablation rates are relatively slow, significantly lengthening procedure times. Further, since formation of the char layer takes place at relatively low rates, undesirable thermal damage to deeper tissue layers may occur. In contrast, it has been found that a macropulsed beam, such as that generated by laser 102, promotes rapid formation of a char layer even at moderate output energy levels, thereby helping to accelerate ablation rates and reducing procedure time.

The macropulsing can also increase efficiency because the threshold voltage required for lasing while macropulsing (the operating threshold) is lower than the initial threshold voltage for lasing (cold threshold).

Macropulsing is also more efficient for producing green light because the conversion of infrared light to frequency doubled light increases as the square of the infrared light intensity. The higher peak powers of the macropulsed infrared light leads to higher second harmonic conversion efficiency. For example, at any given time, the input power and output power of a frequency-doubled laser using KTP are related according to $$Po=A(Pi)^2,$$

Where A is an experimentally determined positive constant. This equation relates the peak input power to the peak output power. However, the average input power and output power for a duty cycle of k percent are given by $$<Pi>=k(Pi)$$

and $$<Po>=k(Po)=kA(Pi)^2=A(<Pi>)^2/k,$$

where the brackets "< >" indicate an average value of the enclosed quantity. Thus, decreasing the duty cycle from 100% to 50% (i.e. reducing k from 1 to 0.5) while simultaneously doubling the peak input power Pi results in no change to the average input power <Pi> and a doubling of the average output power <Po>. Pulse modulating or macropulsing using Q-switching, for example, enables reaching higher average output powers with less thermal lensing due to the lower input power.

Additionally, it is possible that the frequency doubling crystal has nonlinearly increasing output power as a function of the input power. In other words the second derivative of the output power with respect to the input power may be positive, in which case the rate of increase of the output power increases with increasing input power. Specifically, in such a case the functional dependence of the instantaneous or peak output power, Po, on the instantaneous or peak input power, Pi, is such that $$d^2(Po)/d(Pi)^2>0.$$

When this is true and Po is an increasing function of Pi, the higher peak input power results in a more efficient laser because the ratio of the output to input power increases.

By way of a non-limiting example, prostate tissue 104 may be efficiently and rapidly ablated when laser 102 is operated at an output power of 100 watts, a pulse duration of 1–50 milliseconds, and a wavelength of 532 nanometers.

In accordance with a second method embodiment of the invention, laser system 100 may be utilized to ablate other types of tissue 104. Treatment of tissue 104 is performed in a manner substantially identical to the technique for treating BPH disclosed above. The clinician may utilize an endoscope or similar instrument to guide the distal end and tip 140 of optical fiber 106 into alignment with the prostate tissue 104. Laser system 100 is then operated in the macropulsed mode so that laser light having the pulsed waveform depicted in FIG. 3 is generated by laser 102 and delivered through optical fiber 106 to tissue 104. To achieve adequate results, laser system 100 is adjusted to emit a beam having a pulse duration between 0.1 and 500 milliseconds, and an output power of at least 20 watts. Upon vaporization of the required volume of tissue 104, (which may be assessed via an imaging channel contained in the endoscope), the output beam of laser 102 is turned off.

Figure 4:
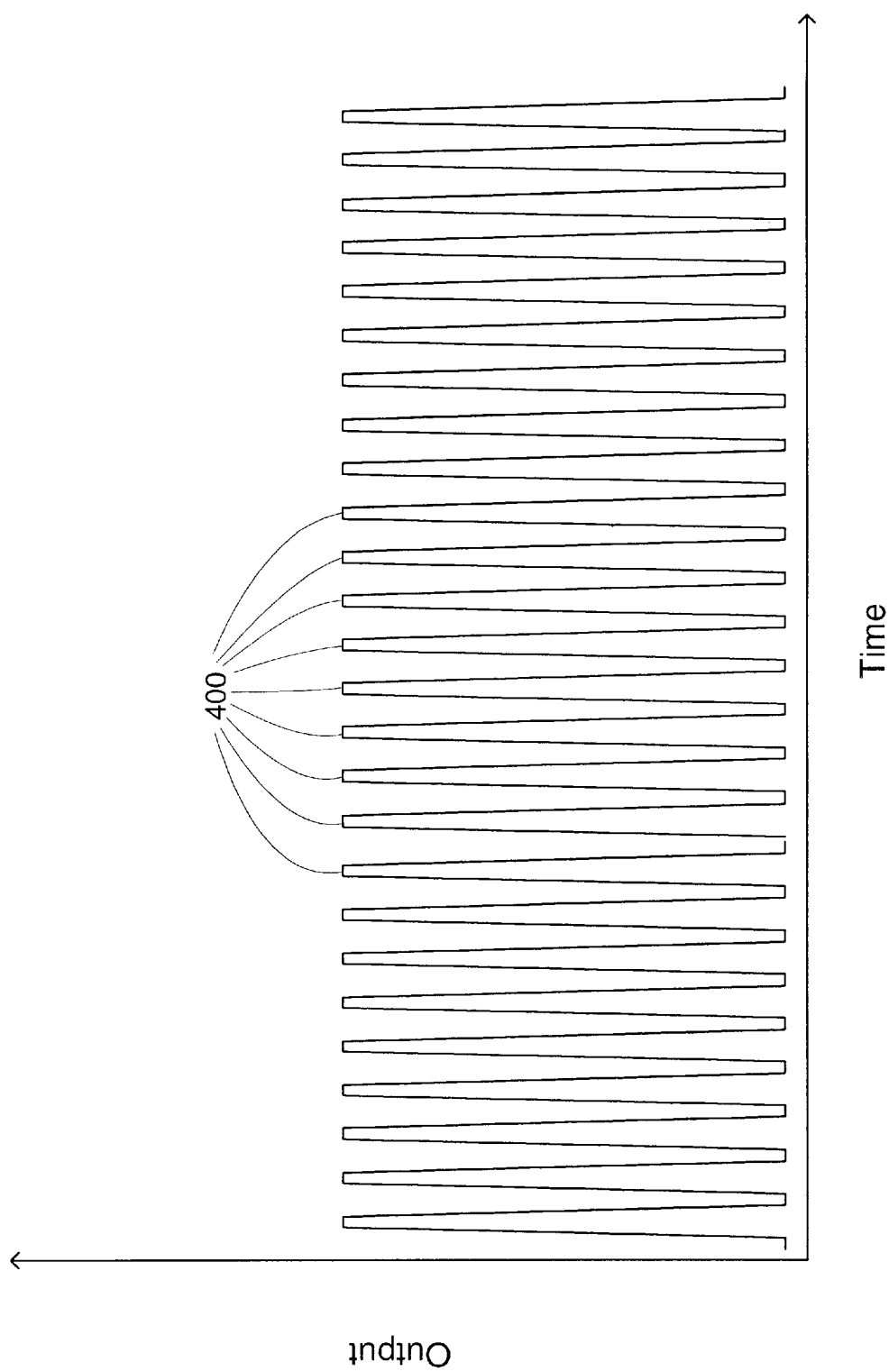
FIG. 4 depicts an exemplary output waveform of the FIG. 1 laser when the laser is operated in a quasi-CW mode.

In a third method embodiment of the invention, treatment of BPH is effected by operating laser 102 in a quasi-CW mode at an output power greater than 60 watts. The increased denaturization of the tissue is dramatic with increases in power, suggesting a threshold effect. As depicted in FIG. 4, laser 102 generates a continuous train of Q-switched micropulses 400 when operated in quasi-CW mode. The laser light is then delivered via optical fiber 106 to targeted tissue 104. Operation in a quasi-CW mode at powers above 60 watts facilitates formation of char and consequent rapid ablation rates, whereas operation in a quasi-CW mode at powers below 60 watts forms char more slowly and causes more thermal damage to underling tissue.

A fourth embodiment of this invention is to produce a high power, high beam quality laser that can project high power density laser light onto tissue. To do this the number of transverse optical modes supported by the resonator needs to be kept as low as possible.

Small $M^2$ and high average powers can be achieved by reducing the degree of thermal lensing in the laser element. Using laser diodes as the excitation source is one effective way of greatly reducing both the size of the lasing element and the thermal gradient responsible for creating the thermal lens. The reason for this is that while 2–10% of the light produced from a flashlamp or arclamp is converted into useful laser light 30–60% of the light emitted from laser diodes can be converted to laser light. Since the energy that is not converted to laser light is converted into heat, laser diodes deposit significantly less heat in the lasing element and as a consequence create a less powerful thermal lens. In this manner laser diodes can be used to pump crystalline laser elements or fiber lasers to produce high beam quality lasers. Slab and waveguide lasers that can be pumped by laser diodes, arclamps, or flashlamps are another method of creating low $M^2$ lasers. This is because the thermal gradient produced in slab lasers is linear across the thin dimension of the slab and not radially dependent in contrast to a typical cylindrical lasing element. The linear thermal gradient does not produce a thermal lens resulting in low $M^2$ values.

For example, as a result of the low $M_2$ some embodiments of this invention are capable producing laser light that upon exiting a flat end of a fiber having a diameter of 600 μm has a divergence of 15.3° or lower; 15° or lower; 10° or lower; or 5° or lower, and the power density can be 13,400 watts per centimeter or greater.

While the invention has been particularly shown and described with reference to preferred embodiments thereof, it will be understood by those skilled in the art, that various changes in form and details may be made therein without departing from the spirit and scope of the invention, as defined by the appended claims.

What is claimed is:

1. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted tissue through an optical fiber, wherein the optical fiber terminates in a side-firing probe emitting the laser light in a direction transverse to the longitudinal axis of the optical fiber.

2. The method of claim 1, wherein the light is of a wavelength that is better absorbed by human tissue than by a substance in an intermediate position between the tissue and a device used to deliver the laser light to the tissue.

3. The method of claim 1, wherein the output power density of the light delivered to the targeted tissue is high enough to vaporize the tissue.

4. The method of claim 1, wherein the laser light has a repetition rate of between 1 Hertz and 500 Hertz.

5. The method of claim 1, wherein the laser element is fabricated from neodymium doped YAG (Nd:YAG).

6. The method of claim 1, wherein the pump radiation source is a flash lamp.

7. The method of claim 1, wherein the tissue is soft tissue and the laser light has an average power exceeding 20 watts.

8. The method of claim 7, wherein the laser light has a repetition rate of between 1 and 500 Hertz.

9. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted tissue, wherein the laser further comprises a frequency doubling element.

10. The method of claim 9, wherein the step of delivering the laser light further comprises transmitting the laser light through an optical fiber.

11. The method of claim 9 wherein the frequency doubling element is fabricated from potassium-titanyl-phosphate (KTP).

12. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted tissue, further comprising the step of Q-switching the laser to produce a train of micropulses, each micropulse train collectively form a pulse.

13. The method of claim 12, wherein the step of delivering the laser light comprises transmitting the laser light through an optical fiber.

14. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted tissue; wherein the pump radiation source is a laser diode.

15. The method of claim 14, wherein the step of delivering the laser light further comprises transmitting the laser light through an optical fiber.

16. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted tissue; wherein the pump radiation source is an arc lamp.

17. The method of claim 16, wherein the step of delivering the laser light further comprises transmitting the laser light through an optical fiber.

18. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted soft tissue, and the laser light has an average power exceeding 20 watts, wherein the laser has a frequency doubling element.

19. The method of claim 18, wherein the step of delivering the laser light further comprises transmitting the laser light through an optical fiber.

20. A method for treating benign prostatic hypertrophy (BPH), comprising:
   providing a solid-state laser emitting light with a wavelength of 200 to 1000 nm having a laser element positioned to receive pump radiation from a pump radiation source;
   modulating the pump radiation source to cause the laser element to emit laser light having pulse duration between 0.1 and 500 milliseconds and pulse frequencies between 1 and 500 Hz; and
   delivering the laser light to targeted soft tissue, and the laser light has an average power exceeding 20 watts, further comprising Q-switching the laser to produce a train of micropulses, each micropulse train collectively form said pulse.

21. The method of claim 20, wherein the step of delivering the laser light further comprises transmitting the laser light through an optical fiber.

22. A method for treating benign prostatic hypertrophy (BPH), comprising:
providing a solid-state laser emitting light of a wavelength of 200 to 1000 nm having a laser element positioned to receive pump radiation from a pump radiation source and
the laser has a beam quality (M2) that is less than or equal to 100 and
delivering the laser light to prostate tissue.

23. The method of claim 22 wherein the light is of a wavelength that is better absorbed by human tissue than by a substance in an intermediate position between the tissue and a device used to deliver the laser light to the tissue.

24. The method of claim 22 wherein the output power density of the light delivered to the targeted tissue is high enough to vaporize the tissue.

25. The method of claim 22, wherein said delivering the laser light comprises transmitting the laser light through an optical fiber.

26. The method of claim 25, wherein the optical fiber terminates in a side-firing probe emitting the laser light in a direction transverse to the longitudinal axis of the optical fiber.

27. The method of claim 22, wherein the laser further comprises a frequency doubling element.

28. The method of claim 27 wherein the frequency doubling element is fabricated from potassium-titanyl-phosphate (KTP).

29. The method of claim 22 wherein the laser element is fabricated from neodymium doped YAG (Nd:YAG).

30. The method of claim 22, further comprising Q-switching the laser to produce a train of micropulses, each micropulse train collectively comprising a pulse.

31. The method of claim 22 wherein the pump radiation source is a flashlamp.

32. The method of claim 22 wherein the pump radiation source is an arclamp.

33. The method of claim 22 wherein the pump radiation source is a laser diode.

34. The method of claim 22 wherein the tissue is soft tissue and the laser light that is output has an average power exceeding 20 watts.

35. The method of claim 34, wherein said delivering the laser light comprises transmitting the laser light through an optical fiber.

36. The method of claim 34, wherein the laser has a frequency doubling element.

37. The method of claim 34, further comprising Q-switching the laser to produce a train of micropulses.

38. The method of claim 22, wherein the step of delivering the laser light further comprises transmitting the laser light through an optical fiber.

39. A method comprising:
irradiating soft tissue of a body with coherent radiation from a laser having
a pump radiation source that does not produce enough heat in a lasing element to create a significant amount of thermal lensing in the lasing element
a wavelength such that the radiation is preferentially absorbed by the tissue rather than a fluid; and
a temperature that is generated by the lasing element that is low enough so that a number of modes of the radiation are few enough so that an average power density is high enough to ablate the tissue leaving less thermal damage than a 60 Watt laser emitting a wavelength near 532 nm.

40. The method of claim 39, wherein an absorptive layer of denatured tissue is formed on the tissue that absorbs the coherent radiation.

41. The method of claims 39, wherein the radiation is pulsed.

42. The method of claims 39, wherein the radiation has micro pulses grouped into macro pulses.

43. The method of claim 39, further comprising frequency converting the radiation prior to irradiating the tissue.

44. The method of claim 39, wherein the radiation has an intensity profile that has a high enough beam quality so that an ablative power density can be projected on the tissue.

45. The method of claim 39, wherein the radiation has an intensity profile that has a sufficient beam quality so that the radiation is able to ablate the tissue
without being so high as to be absorbed by water, and
without causing significant damage to tissue significantly deeper in the body than the tissue ablated.

* * * * *